(12) United States Patent
Perraut et al.

(10) Patent No.: US 7,396,650 B2
(45) Date of Patent: Jul. 8, 2008

(54) METHOD FOR DOSING A BIOLOGICAL OR CHEMICAL SAMPLE

(75) Inventors: François Perraut, Saint Joseph de Rivière (FR); Emmanuelle Schultz, St. Egreve (FR)

(73) Assignee: Commissariat a l'Energie Atomique, Paris (FR)

( * ) Notice: Subject to any disclaimer, the term of this patent is extended or adjusted under 35 U.S.C. 154(b) by 0 days.

(21) Appl. No.: 10/560,973

(22) PCT Filed: Jun. 24, 2004

(86) PCT No.: PCT/FR2004/050289

§ 371 (c)(1),
(2), (4) Date: Dec. 14, 2005

(87) PCT Pub. No.: WO2005/001449

PCT Pub. Date: Jan. 6, 2005

(65) Prior Publication Data

US 2006/0121442 A1    Jun. 8, 2006

(30) Foreign Application Priority Data

Jun. 27, 2003    (FR)    ................... 03 50270

(51) Int. Cl.
*G01N 33/53*    (2006.01)
(52) U.S. Cl. .................................... 435/7.1
(58) Field of Classification Search .................. 435/7.1, 435/4, 6, 7, 7.91–7.98; 436/514, 517, 164, 436/171, 172, 800, 805; 356/4.01, 5.04, 356/144, 244
See application file for complete search history.

(56) References Cited

U.S. PATENT DOCUMENTS

| 3,797,937 | A | | 3/1974 | Shofner |
| 4,488,812 | A | * | 12/1984 | Kraft et al. ................ 356/338 |
| 5,097,135 | A | | 3/1992 | Makino et al. |
| 5,827,660 | A | | 10/1998 | Singer et al. |
| 6,071,748 | A | * | 6/2000 | Modlin et al. ............... 436/174 |
| 6,660,147 | B1 | * | 12/2003 | Woudenberg et al. ....... 204/455 |
| 2004/0241748 | A1 | * | 12/2004 | Ault-Riche et al. .......... 435/7.1 |

OTHER PUBLICATIONS

Ulanowski, Z. et al., "Laser diffractometer for single-particle scattering measurements", *Measurement Science and Technology, IOP Publishing*, Bristol, GB, vol. 13, No. 3, pp. 292-296 (Mar. 2002).

* cited by examiner

*Primary Examiner*—Ann Y Lam
(74) *Attorney, Agent, or Firm*—Thelen Reid Brown Raysman & Steiner LLP

(57) ABSTRACT

The invention relates to a method for assaying a biological or chemical sample comprising the following steps:
  illuminating the sample (10) by means of a light beam (17) from a source (11),
  producing an image including the image of the beam (18) diffused by the sample (10),
  analysing the image according to reference criteria,
  extracting information specific to the light/sample beam interaction,
  calculating the assay.

6 Claims, 4 Drawing Sheets

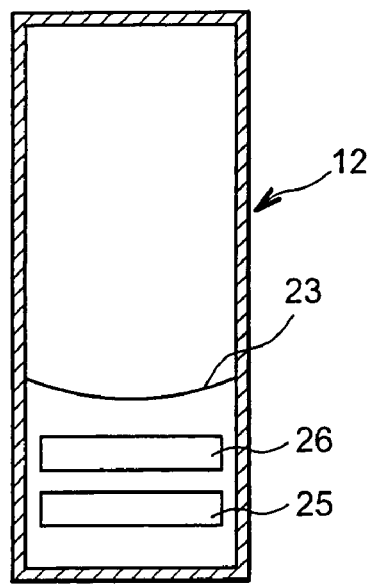
FIG. 4
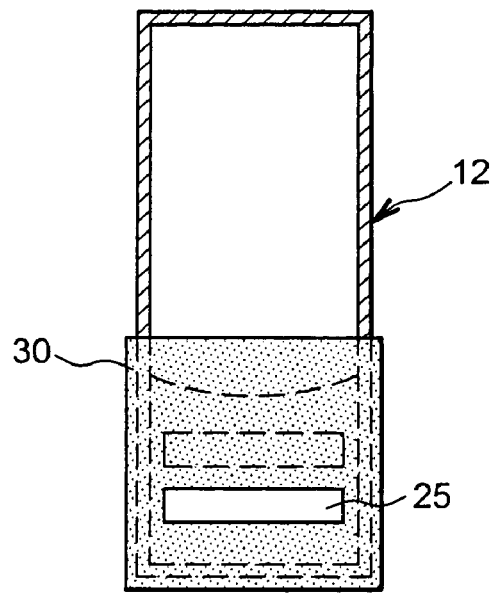 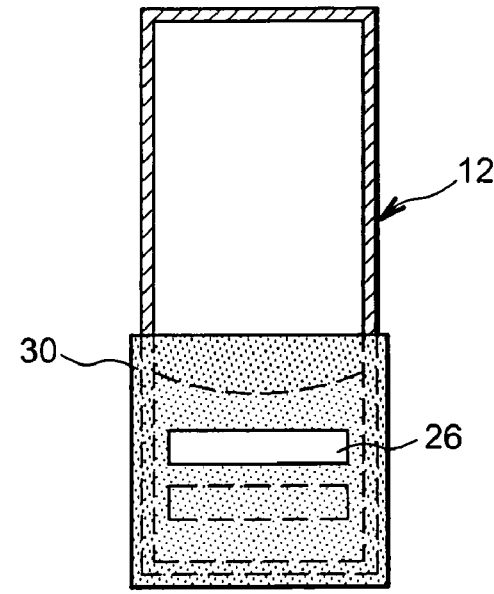
FIG. 5  FIG. 6

METHOD FOR DOSING A BIOLOGICAL OR CHEMICAL SAMPLE

CROSS-REFERENCE TO RELATED APPLICATION

This application claims priority based on International Patent Application No. PCT/FR2004/050289, entitled "Method for Dosing a Biological or Chemical Sample" by Francois Perraut and Emmanuelle Schultz, which claims priority of French Application No. 0350270, filed on Jun. 27, 2003, and which was not published in English.

TECHNICAL FIELD

This invention relates to a method for assaying a biological or chemical sample.

The field of the invention is in particular that of measuring the concentration of fluorescent molecules called fluorochromes contained in solutions. Such molecules are used to assay the amount of a given biological species. The number of molecules of this biological species is thus related to the amount of fluorescent molecules. A measurement of the intensity emitted in the excitation of these fluorescent molecules makes it possible to deduce, by calibration of the measuring apparatus used, the number or concentration of biological molecules. Such measurements are routinely used in biology, chemistry and physics.

In the following description, for the sake of simplification, the invention is described in terms of this field of measuring the fluorescence of samples.

PRIOR ART

Many commercial apparatus, such as fluorimeters and spectro-fluorimeters, enable the fluorescence of a solution to be measured. These apparatuses make it possible to obtain a measurement in a chamber of which the shape is variable and depends upon the application.

Other apparatuses for measuring in solution use capillaries as a chamber. These are, for example, measuring systems for an electrophoresis apparatus.

In all of these apparatuses, a sample placed in a chamber, with which a single detector is associated, is measured.

In some spectro-fluorimetry applications, multiple detectors are used. The fluorescent molecule emission spectrum is then dispersed over an image sensor so as to simultaneously measure the energy in all of the wavelengths, which amounts to the use of a single detector for each spectral interval. A plurality of pixels are sometimes associated in the orthogonal direction with that of the dispersion so as to carry out a so-called "binning" operation which enables the signal-to-noise ratio of each spectral measurement to be increased while reducing the readout noise of the detectors with the photon flow. Multiple detectors are also used in some multi-sample apparatuses. The presence of a plurality of samples then requires the use of a plurality of chambers, and the measurement for each sample is performed with an image sensor.

The detection sensitivity of such apparatuses is inadequate to assay small numbers of molecules, typically of the order of the picomole, either for diagnosing a disease or for studying the purity of a solution. Some assay types are even impossible to carry out below a certain concentration: in the field of immunoanalysis (antigen assay), the statistical detection threshold of the prior art, expressed in terms of target concentration, the lowest obtained for a measurement in solution is of the order of one hundred picomoles. Typically, commercial chamber apparatuses do not enable a fluorescence below a target concentration of 1 nM (nanomole) to be measured.

To reduce the detection limit, the light of a laser source can be focused into a very small space, as is done in capillary electrophoresis. The sample then passes into a capillary of a few hundred micrometers of diameter. The detection limit obtained is of the order of the nM, as described in reference document [1] at the end of the description.

Such a marker detection limit exists in a complex system comprising integrated confocal optics searching the interior of a capillary, as described in reference document [2].

The measuring systems use capillaries not allowing for a very high sample rate, for example, of one dozen to one hundred microlitres/minute. It is therefore impossible to perform a measurement on a high-volume sample. The resulting selection reduces the molecular sampling and increases the detection threshold. For example, if it is possible to detect the presence of a single molecule by fluorescence correlation techniques, as described in reference document [3], the probe volume is very small, of the order of a femtolitre. Detecting a molecule in such a volume gives a detection limit of the order of a nM.

To increase the power density in the excited volume, the excitation light can be focused. As the fluorescence emission is nearly proportional to the amount of energy received in the excitation, the increase in power density enables the number of photons emitted in fluorescence to be increased. For a well-designed measuring system, as is the case for most commercial instruments, the number of measured photons is greater and the uncertainty with regard to this measurement is lower. This uncertainty varies as $1/\sqrt{N}$ where N is the number of photons transformed into electrons during the conversion by the detector. This justifies the choice of an increase in power density in the excited volume. However, a high power density is accompanied by a photo-extinction, which is all the more rapid as the light energy is high. For the measurement of a very low concentration of fluorescent molecules, it is then necessary to expose this volume for an amount of time greater than the photobleaching time, which corresponds to a property of the fluorescent molecules consisting of stopping the emission of light at the end of a certain time period. It is then impossible to collect enough photons to reach the required detection threshold.

Factors that limit the detection threshold lie in the autofluorescence of liquids, which is an intrinsic fluorescence of these media, and in the Raman scattering. The level of emitted light indeed reduces detection performance because the photoluminescence "offset" of the buffer used is of the same nature as the signal, i.e. "specific", to be detected. If the measuring system is only limited by the "Schottky noise", also called "photon noise", then the smallest statistically measurable signal $S_{min}$ is equal to $3\times\sqrt{Offset}$, where "Offset" is a measurement expressed in primary electrons (electrons resulting directly from the conversion of photons by a photocathode in the case of a photomultiplier or a semiconductor surface) and 3 is an arbitrary factor that guarantees 99% discrimination between $S_{min}$ and Offset. To solve such a problem, the solutions of the prior art consist of:

1) a careful selection of liquids,
2) a selection of the marker,
3) an increase in the measuring time in order to accumulate photons,
4) an increase in the excitation power in order to collect more photons.

However, the main factor limiting the detection threshold is the non-reproducibility of the measurements, which, for low signal levels, becomes dominant very quickly. This non-reproducibility essentially arises out of a poor mechanical repositioning of the measuring chamber and the light that is collected by the liquid meniscus in said chamber and which is randomly directed into the space.

A solution for reducing this type of non-reproducibility consists of performing the injection in the chamber of a greater volume of solution. However, such an injection is adequate for obtaining good sensitivity. Moreover, it is not always possible or desirable to work with large volumes.

The mechanical positioning is not easy to improve. In addition, in such a solution, variations caused, for example, by ambient lighting and the variation in the form of the meniscus are not addressed.

Another solution for reducing this type of non-reproducibility consists of using chambers including a transparent "black" glass window, which corresponds to the zone taken into consideration for the measurement. This solution, however, reduces the photon flow collected by the measuring system, and therefore increases the detection limit. Moreover, it does not enable the "offset" variations to be known, which can be caused by a change in the ambient light, by poor surface conditions on the sides of the chamber (soiling, scratches, and so on), or by a diffusion from the meniscus and the walls.

Thus, these various solutions of the prior art do not allow for good sensitivity or good reproducibility of the measurement.

The aim of the invention is to overcome these disadvantages by proposing a new method for assaying a biological or chemical sample that uses a device for spatial recording of the image of interaction between the light coming from a source and this sample as a means for selecting the necessary information.

DESCRIPTION OF THE INVENTION

The invention relates to a method for assaying a biological or chemical sample, comprising the following steps:
  optionally placing the sample in a chamber of which all of the sides are transparent,
  lighting the sample by means of a light beam from a source,
characterised in that it also comprises the following steps:
  producing an image including the image of the light diffused by the sample,
  analysing the image according to reference criteria,
  extracting information specific to the light/sample beam interaction,
  calculating the assay.

In this method, the diffusion can be Raman scattering, fluorescence scattering, molecular diffusion or particle scattering. The analysis can consist of a study of the spatial structure of the image and of the distribution of light energy in this image. The assay can be calculated with respect to a calibration between the measurement of light energy and the sample concentration or amount. The assay can also be calculated with respect to the analysis of the kinetics of the biological or chemical reaction.

Advantageously, in this method, a first zone of interest around the excited volume zone, and a second zone of interest next to this first zone are defined, and the specific signal is measured by carrying out the subtraction between the sum of all of the pixels of the first zone and the sum of all of the pixels of the second zone.

The invention has the following advantages:
  It makes it possible to obtain a much lower experimental detection limit than that of the conventional systems.

It makes it possible to perform an assay using a large volume of solution with a high flow rate, and therefore to consider applications such as the analysis of river waters and building ventilation systems.

It does not require the light to be focused in a small volume. The photobleaching of the fluorescent molecules is therefore very low.

It makes it possible, due to the shape of the chamber, to simultaneously excite a large number of molecules, which enables numerous photons to be collected.

Neither the autofluorescence nor the Raman scattering of the liquid medium limits the sensitivity of the invention. It therefore makes it possible to work with all commercial markers, thereby reducing the marking constraints.

The non-reproducibility due to the chamber mechanics, cleaning or deterioration of the optical surfaces of the chamber, and the presence of artefacts (bubbles, dust) are no longer a constraint. The invention makes it possible, by image analysis, to reduce and even eliminate these. A shift in the position of the chamber in the measuring system of the invention or a shift in the excitation light of the medium can be fully corrected after measuring the position of the fluorescent trace in the recorded image. Similarly, dust present in the excited volume, which could significantly modify the measurement, is small with regard to the excited volume, and can thus be identified and removed from the measurement without losing the latter, which is impossible to perform with a mono-detector. In the event of deterioration of the optical surfaces of the chamber, which can lead to a modification in the amount of light that actually excites the sample, the invention enables the variations in the effective power to be known and the measurement to be corrected.

The variations in ambient light caused either by the sample or by the environment are compensated by a measurement of any "offsets" in the image, then the removal thereof.

The analysis of the information in an image can be performed on the basis of predetermined elements (shading function, predetermined positions of the various useful zones), or dynamically in order to deal with random and/or unforeseen disturbances by applying image-processing methods (entropy maximisation, neural network).

The dynamics of the assay of the invention, which, for a certain type of measurements, makes it possible to experimentally achieve biological assay dynamics of 2 200, is much higher than that of the prior art, which, for the same type of measurements, is typically between 5 and 10.

The invention can be applied to a number of fields, and, in particular:
  in all of the fields where it is useful to measure a fluorescent solution,
  in biology, and more specifically for the assay of biological molecules or molecules of biological interest: antigens, antibodies, peptides, DNA, cells, bacteria, and so on, for a clinical diagnosis,
  in chemistry (assay),
  in pharmacy: assay of activity, contamination, and so on,
  in physics: search for product traces, fluidic traces, mixture analysis, and so on.

BRIEF DESCRIPTION OF THE DRAWINGS

FIGS. 4 to 6 show a second embodiment of a device implementing the method of the invention.

DETAILED DESCRIPTION OF SPECIFIC EMBODIMENTS

The method of the invention is a method for assaying (measuring a concentration or an amount) of a biological sample or a sample of biological interest (antigens, antibodies, peptides, DNA, cells, bacteria, toxins) or a chemical sample (solvent, dissolved gas, preparation, chemical activity), which can be a solid, a liquid, a gel, and so on.

Figure 1:
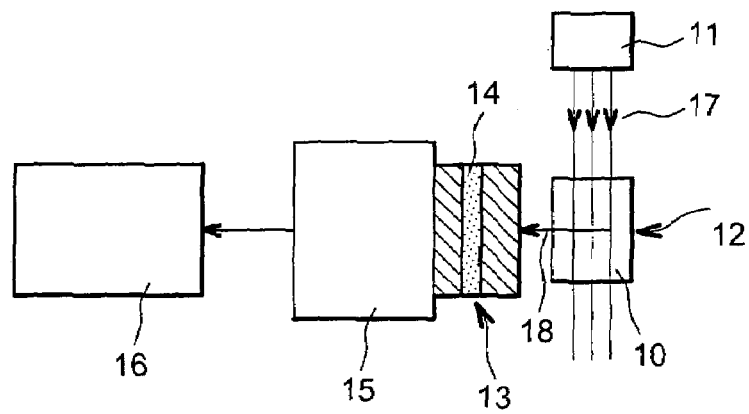
FIG. 1 shows a bottom view of a first embodiment of a device implementing the method of the invention.

In a first embodiment shown in FIG. 1, a sample 10 is illuminated by a light beam 17 coming from a source 11 provided with the fluorochrome used. For example, a 488-nm argon laser can be used for fluorescein or a helium-neon laser at 633 nm can be used for Cy5. The sample 10 is placed in a chamber 12, for example, with a rectangular cross-section, of which all of the sides are transparent. The cross section of this chamber 12 can indeed be rectangular, square, cylindrical or elliptical. An objective system 13, equipped with a blocking filter 14, is mounted in front of a device for recording the spatial structure of an image 15, for example, a CCD camera or a scanning system, connected to a processing component 16. The device 15 that receives the beam 18 diffused by the sample 10 makes it possible to record an image from which a specific measuring signal can be extracted.

The method of the invention includes the following steps:
  illuminating the sample 10 by means of a light beam 17 coming from the source 11, which can be a gas laser, a solid laser, a laser diode, an electroluminescent diode, an organic diode, a spectral bulb such as a halogen, mercury, xenon, or deuterium bulb,
  producing an image of the light beam 18 diffused by the sample 10, wherein the origin of the diffusion can be Raman scattering, fluorescence scattering, molecular diffusion (Rayleigh scattering) or particle scattering (use of nanoparticles),
  analysing the image with respect to references, which analysis consists of examining the spatial structure of the image and the distribution of light energy in this image, wherein said references can be constituted, for example, by the experience of a user or by morphological criteria (form and position of a light trace), photometric criteria (frequency of spatial variations of the light in the image), or statistical criteria (variation of measurement estimators, image entropy),
  extracting information specific to the interaction between the beam 17 and a sample 10, which extraction consists, for example, of arithmetic operations between the image and other images or constants (for example, subtractions, additions, divisions, multiplications), morphological operations (erosion, dilation, binarization, clipping, segmentations, offset correction) or photometric operations (polynomial corrections, convolutions, filters, thresholding),
  calculating the assay with respect to a calibration between the measurement of light energy and the concentration or quality of the biological or chemical sample. This calculation can also be performed by recording the kinetics of the biological or chemical reaction and by analysing this kinetic using methods known to a person skilled in the art.

In the method of the invention, the measurement is performed in an image obtained by the device for recording the spatial structure of an image 15. The invention does not lie in the use of such a device 15, but primarily in:
  the recording of the beam 18 diffused by the sample 10 in the form of an image,
  the extraction of information from this image,
  the adaptive side obtained by the application of an image analysis.

Figure 2:
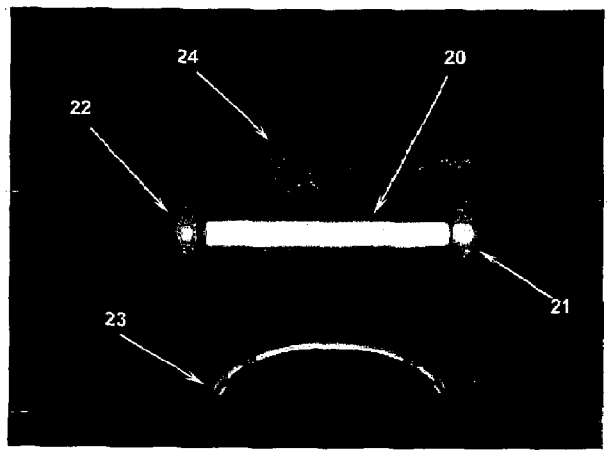
FIGS. 2 and 3 show an image of the chamber obtained with the image-recording device shown in FIG. 1.

FIG. 2 shows the image of the chamber 12 obtained with the device for recording the spatial structure of an image 15. The chamber can have smaller dimensions than those of the image. It can, for example, be replaced by one or more capillaries.

In addition, the light beam can be either smaller or larger than the chamber.

In this image, a plurality of zones can be distinguished:
  an illuminated volume zone 20, which corresponds to the volume of the chamber 12 excited by the beam 17,
  the zone 21 where said beam 17 enters the chamber 12,
  the zone 22 where said beam 17 exits the chamber 12,
  a meniscus zone 23,
  an artefact zone 24.

Figure 3:
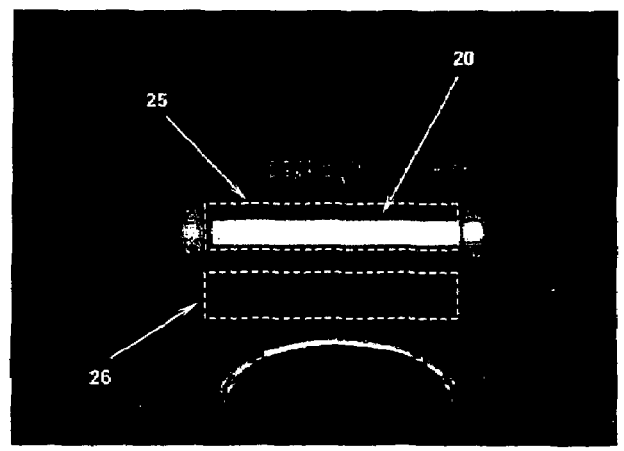

Thus, as shown in FIG. 3, it is possible to define a first region of interest 25 around the illuminated volume zone 20 and a second region of interest 26 next to this zone 25. The measurement of the specific signal is then given by the calculation: $\Sigma RI_1 - \Sigma RI_2$; that is, the subtraction between the sum of all of the pixels of the first region of interest 25 and the sum of all of the pixels of the second region of interest 26.

In FIG. 3, the two regions of interest 25 and 26 have the same size, which is not essential. When these regions do not have the same size, it is simply necessary either to average the grey levels of each region, or to balance the values by the number of pixels.

The image analysis thus represented leads to certain observations:
  The fluorescent trace of the light beam (zone 20) gives the specific signal.
  The meniscus (zone 23), delimiting the liquid from the air, has a strong light. It originates from said trace. The form of this meniscus is highly random. The amplitude of the signal coming from this meniscus is therefore highly variable.
  An artefact (zone 24) can be, for a given assembly, a spring lock washer designed to ensure the proper mechanical positioning of the chamber 12.
  The zones 21 and 22 correspond respectively to the points of entry and exit of the light beam in the chamber 12.

With another adjustment of the display thresholds, it is easier to show the lowest light levels.

The method of the invention makes it possible to improve the variation coefficient (CV) (standard deviation/mean). Indeed, the coefficient CV obtained with the method of the invention is lower than the coefficient CV calculating by obtaining the sum of all of the pixels of a CCD camera, which corresponds to a measurement performed with a mono-detector. The coefficient CV obtained with the method of the invention is of the same order of magnitude as that obtained with a high solution volume, as considered previously in the introduction to said application. This coefficient CV obtained with the method of the invention is lower than that obtained by the measurement in each of the zones of interest 25 and 26. The subtraction of the measurements performed in these two zones of interest makes it possible to correct lighting variations that affect all of the regions. The invention thus makes it possible to perform spatial filtering in the plane that enables the signal containing specific information on the fluorescence to be extracted. Moreover, the invention makes it possible to extract the regions of interest which are truly relevant in an image or a pseudo-image, while a measuring system using a single mono-pixel detector cannot perform such a function.

In a second embodiment, a mono-detector associated with a matrix of pixels with programmable transparency 30 such as a liquid crystal or micro-mirror matrix or any other equivalent system is placed in front of the chamber 12 shown in FIG. 4. This matrix 30 is intercalated between the chamber 12 and the detector via a system for forming images or not. A first measurement is then performed by "opening" the pixels corresponding to the first zone of interest 25, as shown in FIG. 5, then a second measurement is performed by opening the pixels corresponding to the second zone of interest 26, as shown in FIG. 6.

The use of such a matrix 6 with variable transparency makes it possible to avoid the systematic recording of an image, for example, by performing the following steps:

recording the image of the beam diffused by successively opening/closing all of the pixels of the matrix 30 in synchronisation with the measurement carried out by the mono-detector, analysing the image and defining the zone(s) of interest enabling the specific information to be extracted, recording such parameters for a subsequent use, in the analysis of a given sample, performing successive openings of regions defined in the analysis step and recording the results of the measurement for each of these zones, extracting the necessary information, calculating the assay.

Figure 7:
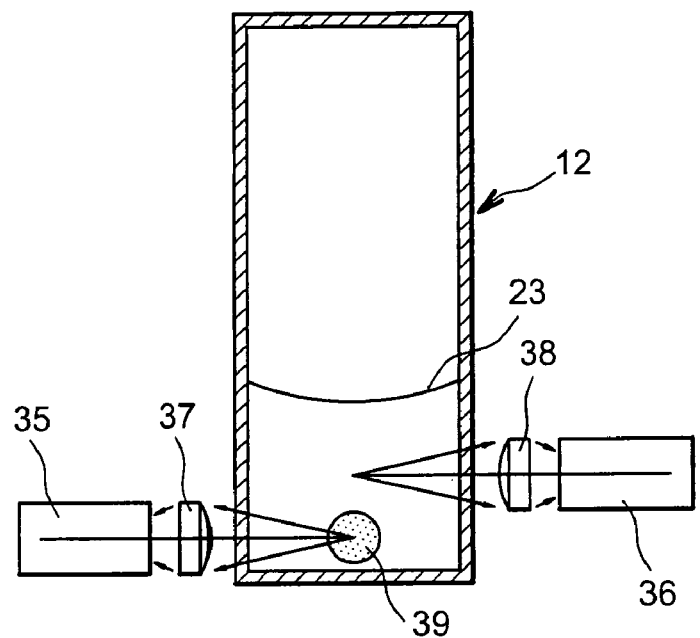
FIG. 7 shows a third embodiment of a device implementing the method of the invention.

In a third embodiment shown in FIG. 7, two mono-pixel detectors 35 and 36 each observe a region of interest 25 or 26. Two image formation means 37 and 38 are placed respectively in front of each of these two detectors 35 and 36. The measurement of the signal coming from the first region of interest 25 is performed with detector 35, and that for the second region of interest 26 is performed with detector 36. The zone 39 shows the front view of the fluorescent trace.

The invention makes it possible to adapt the extraction of the specific signal to experimental conditions. For example, if the chamber has moved between two series of measurements, it is possible, by an automatic analysis of the image, to automatically reposition the regions of interest, an operation that could not be performed with a static system.

EXAMPLES OF EMBODIMENTS OF THE INVENTION

The three examples of embodiments described below correspond respectively to the three embodiments defined above.

Figure 8:
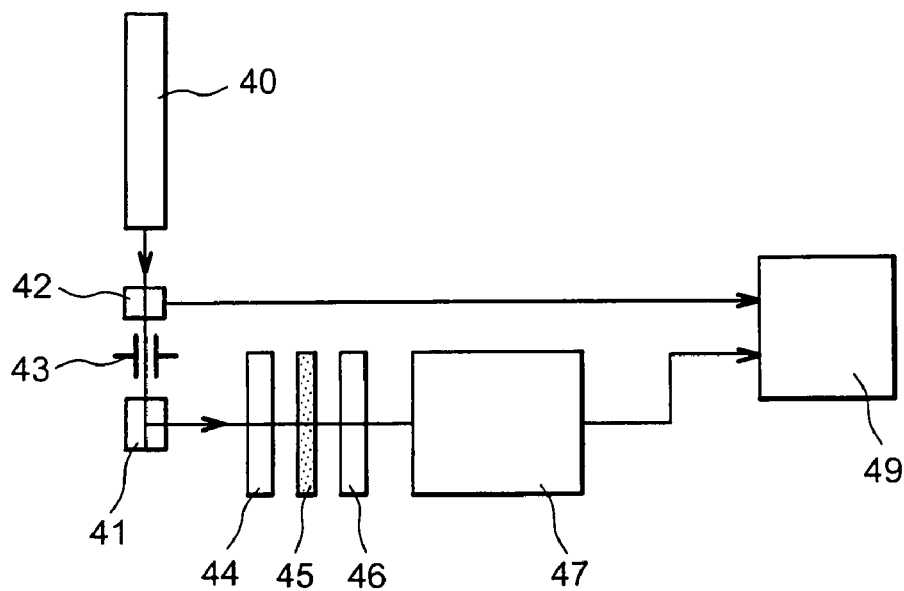
FIGS. 8 to 10 show three examples of an embodiment of a device implementing the method of the invention.

In a first example of an embodiment shown in FIG. 8, a light source 40, for example a laser or an electroluminescent diode, excites, in a chamber 41, the liquid containing fluorescent molecules through optics with a configuration that is not shown, and various accessories such as a shutter 42 and a diaphragm 43. A first objective 44, placed, for example, perpendicularly with respect to the primary direction of the light beam, collects a portion of this light beam, emitted by fluorescent molecules in the chamber 41. A blocking filter 45 is placed behind the first objective 44, just in front of a second objective 46. The association of objectives 44 and 46 enables an image of the chamber 41 to be formed on the image detector 47 which is connected to a command and control system 49. For a chamber 41 with an internal width of 1 cm, this detector 47 can be a detector of 512×512 pixels with a side of 10 µm. The first objective 44 can have a focal length of 50 mm and the second objective 46 can have a focal length of 25 mm.

Figure 9:
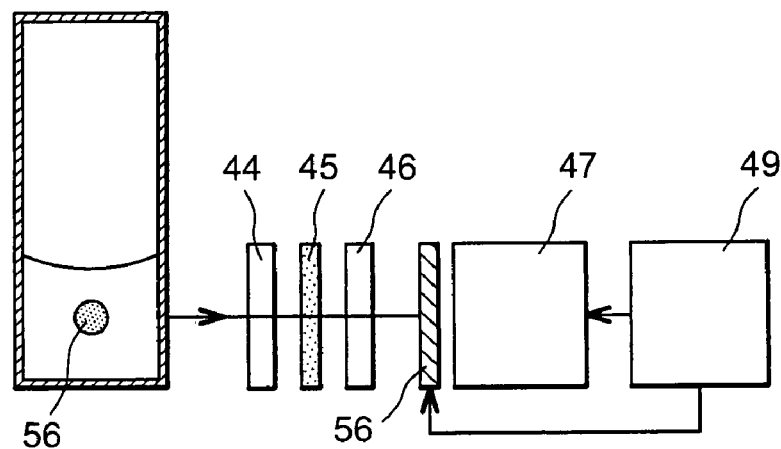

In a second example of an embodiment, shown in FIG. 9, of which the configuration is the same as that of FIG. 8 for excitation, only one detector is used. A matrix 56 with variable transparency, which can be a liquid crystal matrix or a micromirror matrix, acts as a field diaphragm. The matrix 56 can be replaced by a mobile window actuated by a mechanical or electromechanical actuator, for example an electromagnet or an electric motor.

Figure 10:
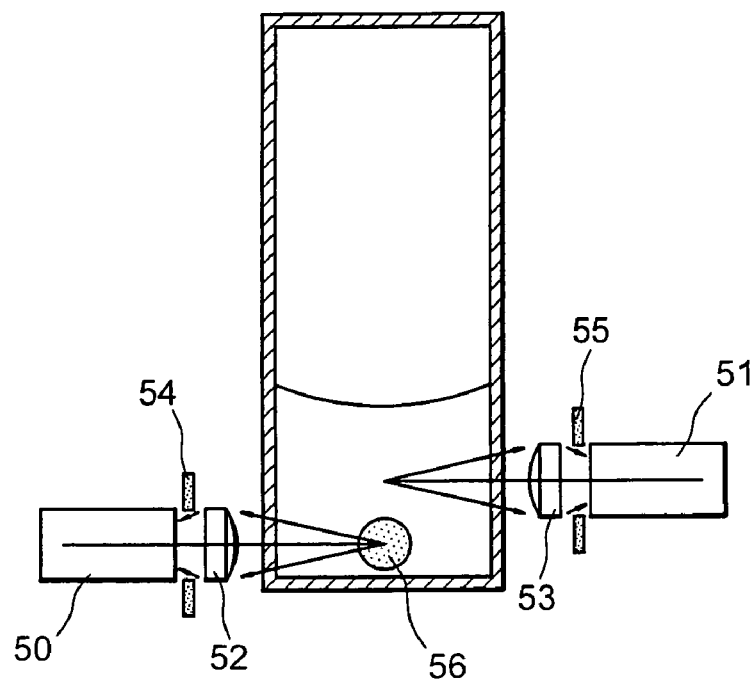

In a third example of an embodiment shown in FIG. 10, the configuration for exciting the inside of the chamber 41 is the same as in FIG. 8, and the configuration for the light collection is the same as that in FIG. 9. Two mono-detectors 50 and 51, for example, offset photomultipliers, enable two different regions of the chamber 41 to be observed. In front of each detector 50 and 51, recapture optics 52 and 53 enable the image of the region of interest to be formed on a field diaphragm 54 and 55, which limits the region observed. A blocking filter can be placed in front of, in or behind the diaphragm. The zone 56 represents the fluorescent trace.

REFERENCES

[1] "Some applications of near-ultraviolet laser-induced fluorescence detection in nanomolar- and subnanomolar-range high-performance liquid chromatography or micro-high performance liquid chromatography" by N. Siméon, R. Myers, C. Bayle, M. Nertz, J. K. Stewart, F. Couderc (2001, Journal of Chromatography A, Vol 913, I 1-2, pages 253-259).

[2] "Performance of an integrated microoptical system for fluorescence detection in microfluidic systems" by J. C. Roulet, R. Volkel, H. P. Herzig, E. Verpoorte, N. F. Rooij, R. Dandliker (2002, Analytical Chemistry, Vol. 74 (14), pages 3400-3407).

[3] "Single molecule detection of specific nucleic acid sequences in unamplified genomic DNA" by A. Castro and J. G. Williams (1997, Analytical Chemistry, Vol. 69 (19), pages 3915-3920).

The invention claimed is:

1. A method of assaying a biological or chemical sample, which comprises:

placing said sample in a chamber having transparent sides;

illuminating the sample using a light beam coming from a source;

producing an image of the light beam diffused by the sample, wherein said image comprises an illuminated volume zone, a light beam point of entry zone, a light beam point of exit zone, a meniscus zone, and an artefact zone;

recording the spatial structure of the image;

examining the spatial structure of the image and distribution of light energy in the image with respect to one or more references, measuring noise created by the step of illuminating the sample, and defining one or more regions of interest so that measuring information can be extracted;

extracting the measuring information, wherein the extracted information is specific to the interaction of the light beam with the sample;

recording the measuring information; and calculating the assay with respect to the measuring information.

2. A method as recited in claim 1, wherein the diffusion is Raman scattering, fluorescence scattering, molecular diffusion or particle scattering.

3. A method as recited in claim 1, wherein the assay is calculated with respect to a calibration between the light energy measurement and the sample concentration or amount.

4. A method as recited in claim 1, wherein the assay is calculated with respect to an analysis of the kinetics of the biological or chemical reaction.

5. A method as recited in claim 1, wherein a first zone of interest around the illuminated volume zone, which corresponds to the volume of the chamber excited by the light beam, and a second region of interest next to this first region are defined, and wherein the measuring information is obtained by subtracting the sum of the signals of all of the pixels of the first region of interest from the sum of the signals of all of the pixels of the second region of interest.

6. A method as recited in claim 1, further comprising deriving the concentration of fluorescent molecules contained in a solution.

* * * * *